United States Patent
Knudsen et al.

(10) Patent No.: US 12,208,062 B2
(45) Date of Patent: Jan. 28, 2025

(54) PHARMACEUTICAL ADAPTOR SYSTEM AND PHARMACEUTICAL KIT SYSTEM

(71) Applicant: AMGEN INC., Thousand Oaks, CA (US)

(72) Inventors: Hans Stenberg Knudsen, Vaerloese (DK); Matias Melander, Copenhagen (DK); Jakob Halkjaer Pedersen, Virum (DK)

(73) Assignee: AMGEN INC., Thousand Oaks, CA (US)

( * ) Notice: Subject to any disclaimer, the term of this patent is extended or adjusted under 35 U.S.C. 154(b) by 575 days.

(21) Appl. No.: 16/072,767

(22) PCT Filed: Feb. 6, 2017

(86) PCT No.: PCT/EP2017/052554
§ 371 (c)(1),
(2) Date: Jul. 25, 2018

(87) PCT Pub. No.: WO2017/134307
PCT Pub. Date: Aug. 10, 2017

(65) Prior Publication Data
US 2019/0083359 A1    Mar. 21, 2019

(30) Foreign Application Priority Data
Feb. 5, 2016  (EP) ..................................... 16154535

(51) Int. Cl.
*A61J 1/20* (2006.01)
*A61M 5/32* (2006.01)
*A61M 39/10* (2006.01)

(52) U.S. Cl.
CPC ............. *A61J 1/2096* (2013.01); *A61J 1/201* (2015.05); *A61J 1/2065* (2015.05); *A61M 5/322* (2013.01);
(Continued)

(58) Field of Classification Search
CPC ........ A61J 1/201; A61J 1/2055; A61J 1/2065; A61J 1/2096; A61M 2039/1044;
(Continued)

(56) References Cited

U.S. PATENT DOCUMENTS 7,470,261 B2 * 12/2008 Lynn .................. A61B 10/0045
604/167.03
2002/0193752 A1   12/2002 Lynn
(Continued)

FOREIGN PATENT DOCUMENTS

WO   WO-2014/099395 A1   6/2014

OTHER PUBLICATIONS

International Search Report for Application No. PCT/EP2017/052554, mailed May 15, 2017.
(Continued)

*Primary Examiner* — Kai H Weng
(74) *Attorney, Agent, or Firm* — MARSHALL, GERSTEIN & BORUN LLP

(57) ABSTRACT

The present invention relates to a pharmaceutical adaptor system. The pharmaceutical adaptor system comprises a syringe assembly having an axial extension and comprising a first end part and a second end part, the first end part having a male tubular projection, the syringe assembly comprising a syringe and a connecting element having a first mechanical connection part, a unit such as a needle, a vial, a catheter or an IV line, and an adaptor providing fluid communication between the syringe and the unit and having a second mechanical connection part configured to engage with the first mechanical connection part in an engagement direction, thereby in fully engaged position preventing further relative axial movement between the adaptor and the male tubular projection, wherein the adaptor comprises a sealing element configured to receive the male tubular projection and pro-
(Continued)

vide sealing between the male tubular projection and the adaptor. The present invention also relates to a pharmaceutical kit system comprising a pharmaceutical adaptor system according to the present invention.

23 Claims, 12 Drawing Sheets

(52) U.S. Cl.
CPC ............ *A61M 39/10* (2013.01); *A61J 1/2055* (2015.05); *A61M 2039/1044* (2013.01); *A61M 2039/1077* (2013.01); *A61M 2207/00* (2013.01)

(58) Field of Classification Search
CPC ...... A61M 2039/1077; A61M 2207/00; A61M 39/10; A61M 5/322
See application file for complete search history.

(56) References Cited

U.S. PATENT DOCUMENTS

| | | | |
|---|---|---|---|
| 2007/0289668 A1 | 12/2007 | Costanzo | |
| 2012/0123382 A1* | 5/2012 | Kubo | A61J 1/2096 604/413 |
| 2012/0265163 A1* | 10/2012 | Cheng | A61J 1/2096 604/415 |
| 2012/0296307 A1* | 11/2012 | Holt | A61J 1/2051 604/407 |
| 2015/0250681 A1* | 9/2015 | Lev | A61J 1/201 604/414 |

OTHER PUBLICATIONS

Written Opinion of the International Searching Authority for Application No. PCT/EP2017/052554, mailed May 15, 2017.

* cited by examiner

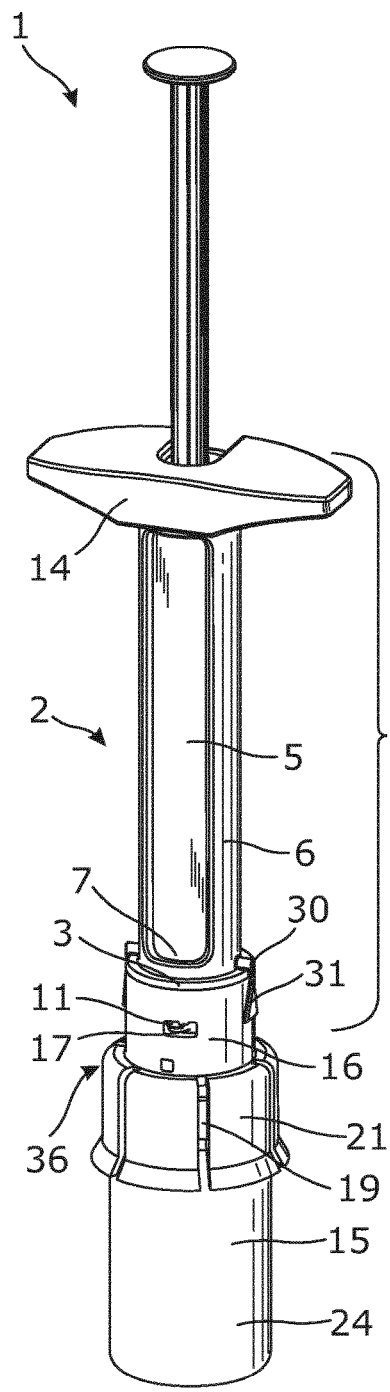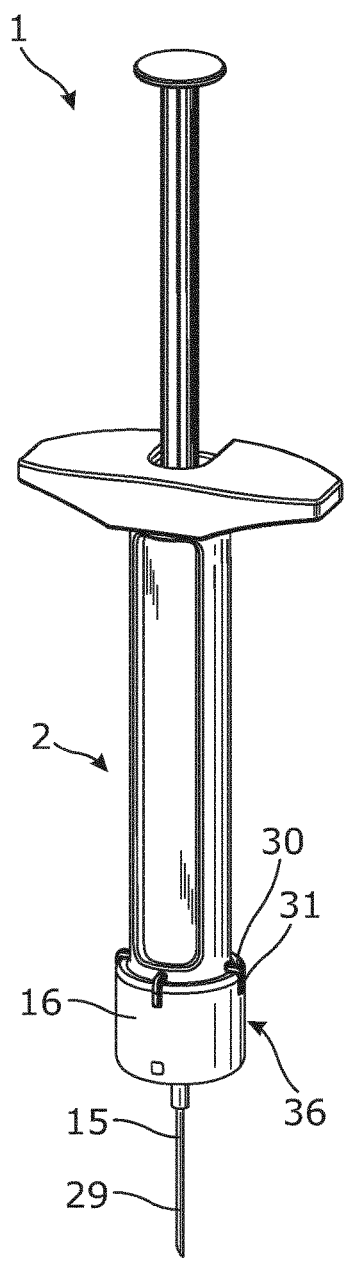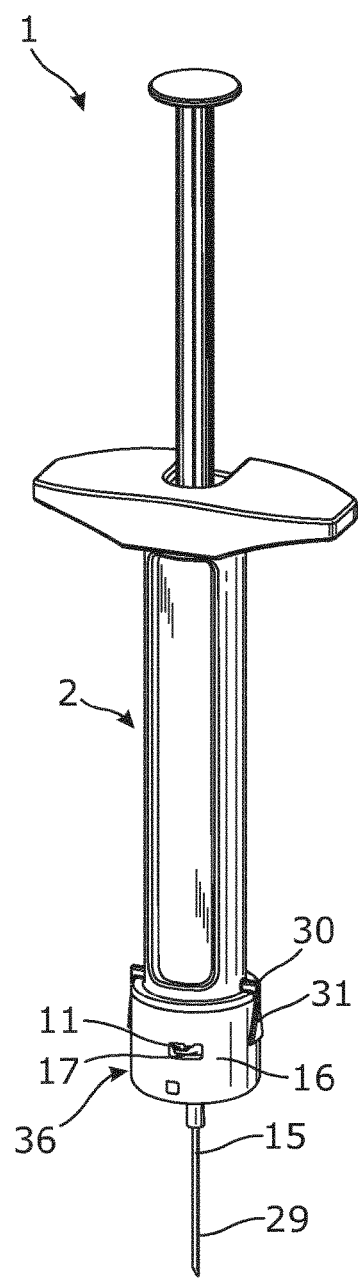
Fig. 2A
Fig. 2B
Fig. 2C

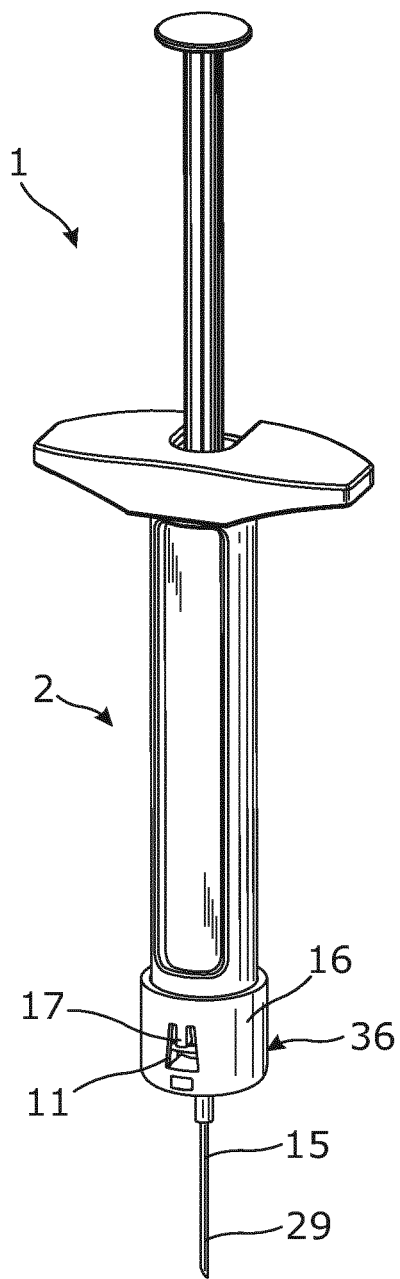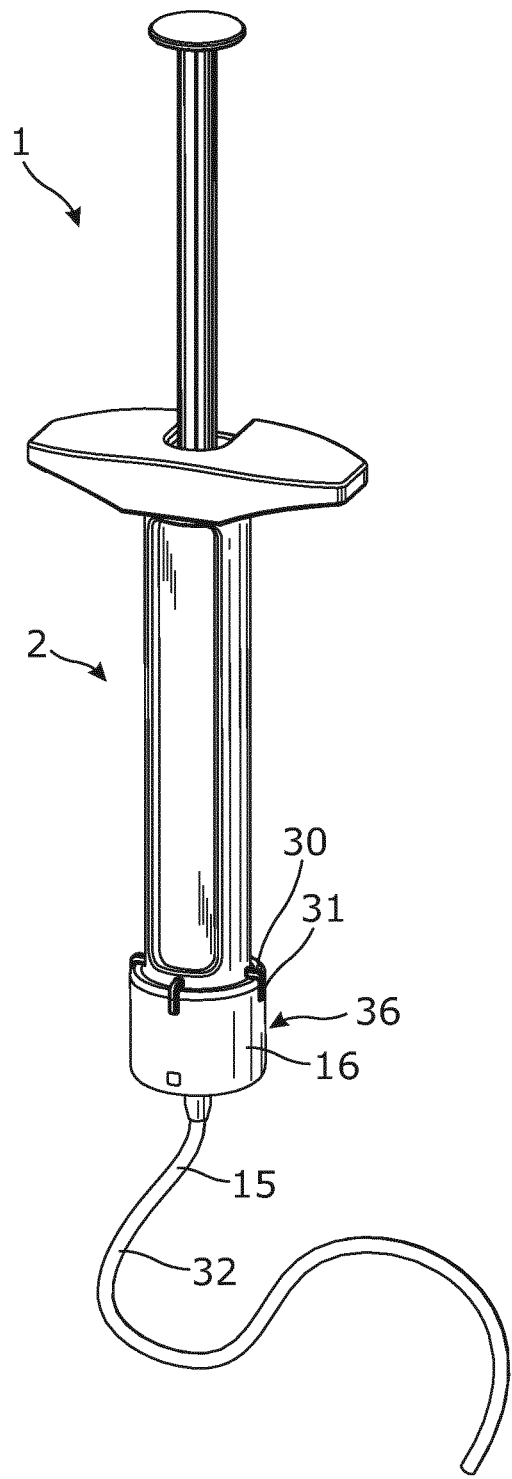
Fig. 2D
Fig. 2E

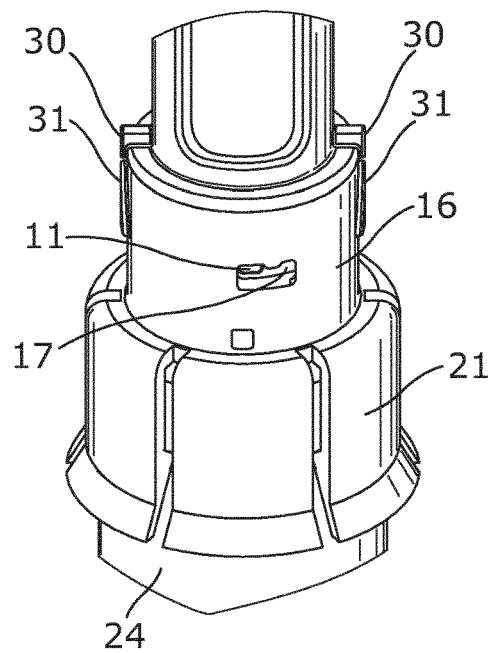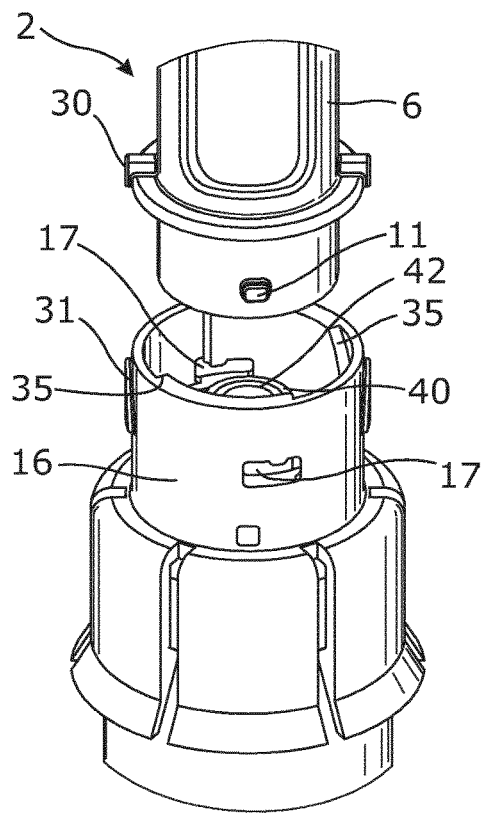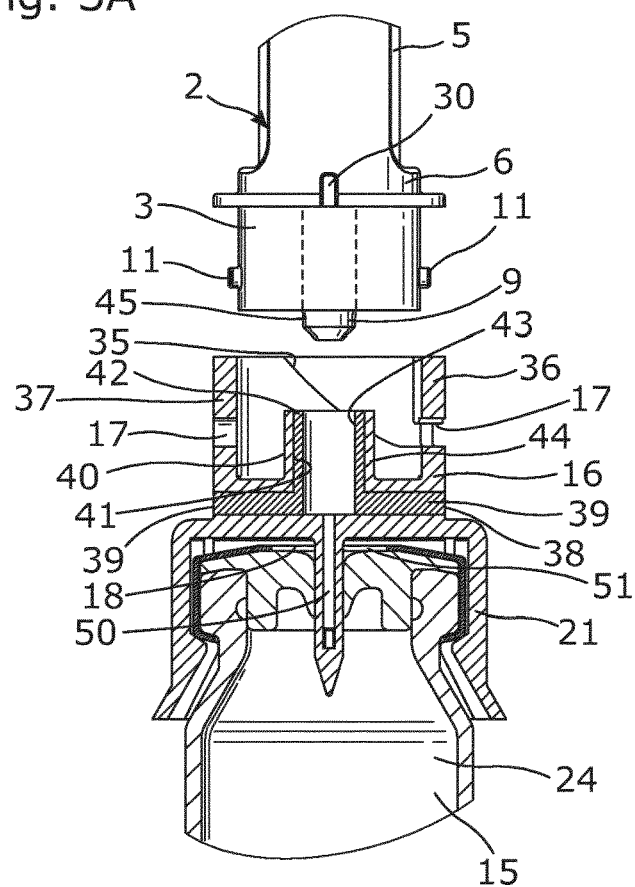
Fig. 3A
Fig. 3B
Fig. 3C

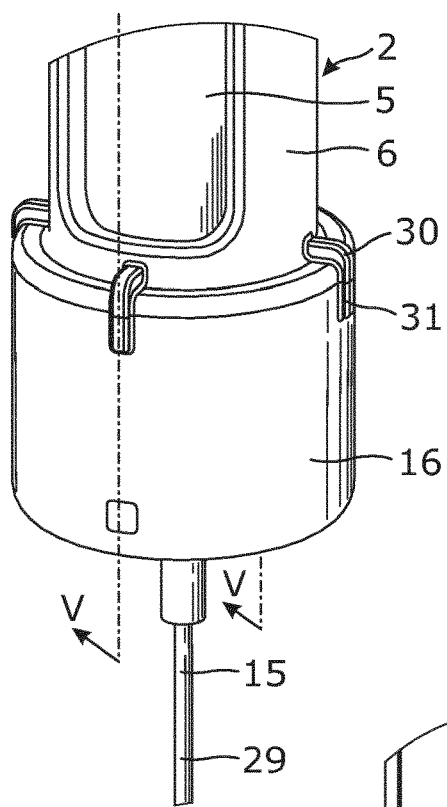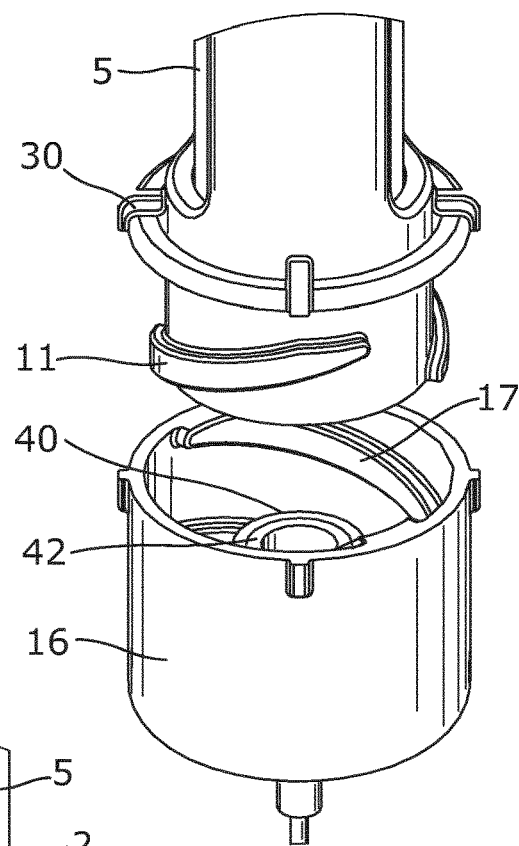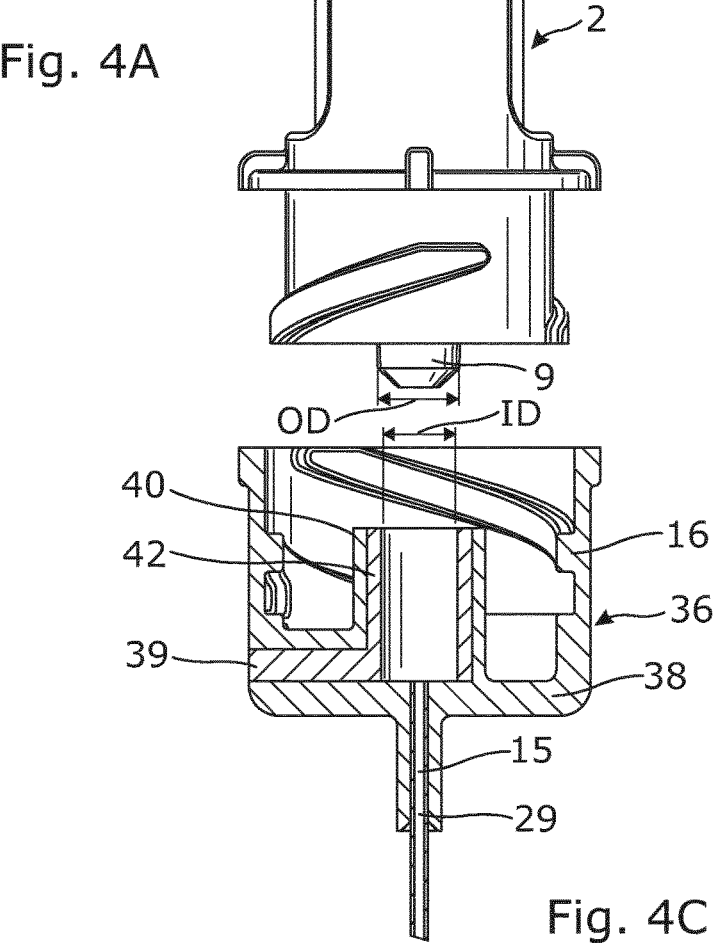
Fig. 4A
Fig. 4B
Fig. 4C

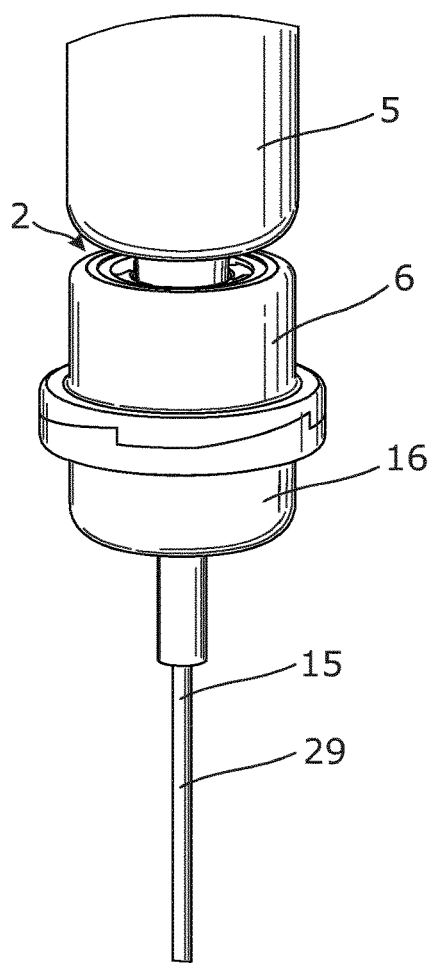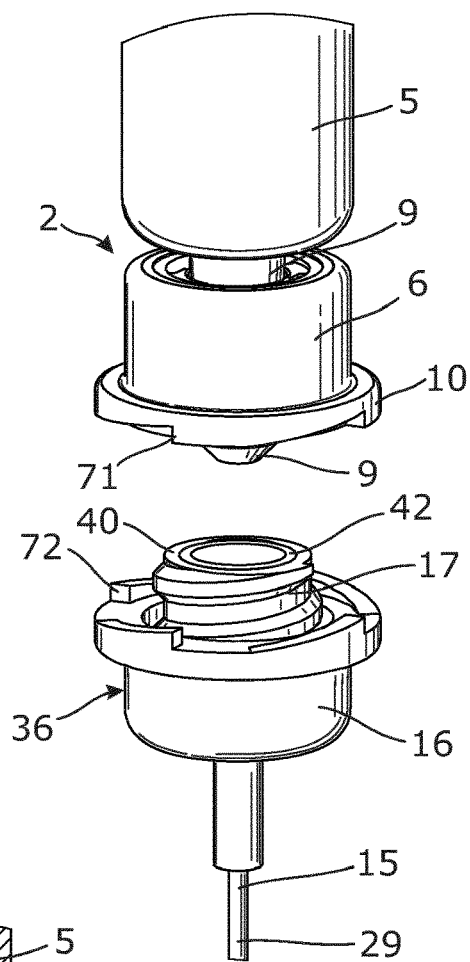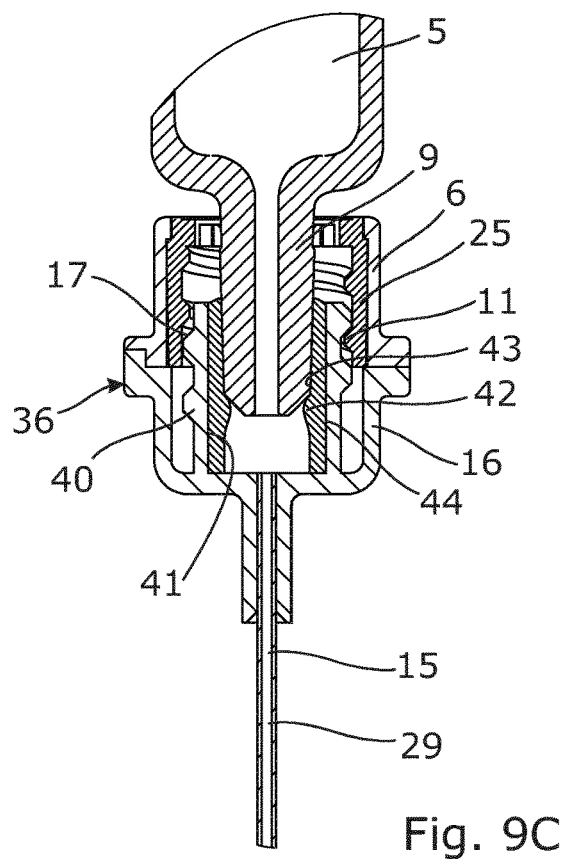
Fig. 9A
Fig. 9B
Fig. 9C

PHARMACEUTICAL ADAPTOR SYSTEM AND PHARMACEUTICAL KIT SYSTEM

CROSS-REFERENCE TO RELATED APPLICATIONS

This application is a United States national phase of International Patent Application No. PCT/EP2017/052554, having an international filing date of Feb. 6, 2017, which claims the priority benefit of European Patent Application No. 16154535.5, filed Feb. 5, 2016. The entire contents of International Patent Application No. PCT/EP2017/052554 and European Patent Application No. 16154535.5 are expressly incorporated herein by reference for all purposes.

FIELD OF THE INVENTION

The present invention relates to a pharmaceutical adaptor system and to a pharmaceutical kit system comprising such pharmaceutical adaptor system.

BACKGROUND ART

When transferring fluid from one container to another container, the risk of leakage and spilling of fluid during the process is present. In controlled environments the risk may be controlled because empirical knowledge has led to greater caution being taken during the critical stages of the transfer process. However, when performing self-administration, the user carrying out the fluid transfer is not a professional with extensive empirical background. As an example, drugs that rely on reconstitution handled by the patient or in general administration by other inexperienced users need secure handling of fluid transfers. Often the diluent needs to be transferred to a syringe from a vial before mixing the medication and diluent.

Often, when glass syringes are used, a problem occurs of ensuring a fluid tight connection during the transfer of fluid from or to the syringe from or to the vial, needle, catheter or an intravenous line (IV line). The problem has even given rise to the Federal Drug Administration (FDA) giving remarks to companies to correct these deficiencies and ensure a fully fluid tight connection between the glass syringe and the device to or from which fluid needs to be transferred.

In general, various couplings are used when dispensing or administering medicine fluids. Luer couplings, e.g. Luer locks and Luer tapers, are well known in various medical and drug administering and dispensing situations. Because the standard is understood worldwide and results in economical, reliable and inexpensive components, it is employed in thousands of medical devices worldwide.

However, the increasing demand for home administration of drugs has increased the need to develop couplings such as the Luer couplings for safe transfer of fluid medicaments even further. This is due to the fact that home users are less familiar with the best use of the couplings, e.g. a Luer coupling. Hence home user need to be able to rely more on the actual product itself to support a correct coupling of various parts when transferring fluids. Previously, drugs for home administration were often delivered in "ready to use" systems, requiring a minimum or no need for assembly by the user, but increasingly the user, e.g. the patient, needs to handle, e.g. assemble and/or disassemble, the pharmaceutical administration systems themselves prior to using them. This need for assembling/disassembling may be due to various reasons, e.g. because reconstitution is needed, or due to repeated use of a part of the system. The correct assembly is important due to increasingly more expensive drugs being administered at home as well as drugs being administered in increasingly smaller volumes. Also, more vital medicine is administered at home. Therefore it is more and more necessary to ensure that no medicine is lost and that correct amounts are dispensed.

Hence, there is a need for a pharmaceutical adaptor system that provides certainty for the user that the system is correctly assembled and that a safe fluid communication is established.

SUMMARY OF THE INVENTION

It is an object of the present invention to wholly or partly overcome the above disadvantages and drawbacks of the prior art. More specifically, it is an object to provide an improved system for transferring fluid from a glass syringe to or from a needle, vial or catheter.

The above objects, together with numerous other objects, advantages and features, which will become evident from the below description, are accomplished by a solution in accordance with the present invention by a pharmaceutical adaptor system comprising:

a syringe assembly having an axial extension and comprising a first end part and a second end part, the first end part having a male tubular projection, the syringe assembly comprising a syringe and a connecting element having a first mechanical connection part, a unit such as a needle, a vial, a catheter or an IV line, and an adaptor providing fluid communication between the syringe and the unit and having a second mechanical connection part configured to engage with the first mechanical connection part in an engagement direction, thereby in fully engaged position preventing further relative axial movement between the adaptor and the male tubular projection, wherein the adaptor comprises a sealing element configured to receive the male tubular projection and provide sealing between the male tubular projection and the adaptor.

In this way it is achieved that the axial tolerances of the length of the syringe are absorbed by the sealing element. Furthermore it is achieved that a consistent user feedback is provided, letting the user know that a correct assembly is achieved.

The sealing element may have an inner face configured to abut an outer face of the male tubular projection. In this way it is achieved that different positions of the male tubular projection in relation to the sealing element obtain the same sealing properties.

Moreover, the sealing element may be a tubular element having a thickness and a length along the axial extension, said axial extension being larger than the thickness. In this way the sealing element is able to obtain different sizes of the male tubular projection of the syringe.

The sealing element may be an insert made of an elastomer such as Silicone, PDM or natural rubber.

The inner face of the sealing element may comprise an annular projection. In this way the sealing element is able to receive a large range of male tubular projections. The annular projection may be a lip.

The annular projection of the sealing element may be arranged near the end section or rim of the sealing element, i.e. the section from which the male tubular projection of the syringe is inserted. In this way it is achieved that a firm fluid tight connection is achieved prior to inserting the male tubular projection to the full depth of the sealing element. The annular projection may be arranged in the first third of the depth of the sealing element seen in the insertion direction of the male tubular element. In this way the annular projection is substantially the first part of the inner surface of the sealing element to receive the male tubular projection.

The annular projection of the sealing element may taper in the direction of insertion of the male tubular projection, i.e. the annular wall of the sealing element may be thinner towards the "inner passage surface".

The pharmaceutical adaptor system may comprise a distinct stop independent from the Luer connection, ensuring that the parts assembled are stopped before the full relative axial movement of the parts is achieved. In other words, compared to a traditional Luer connection, the present pharmaceutical adaptor system may provide a stop for further rotation of the Luer coupling prior to the full assembly via the Luer coupling.

Further, the sealing element may be resiliently configured to provide an axial force opposite the engagement direction upon compression of the sealing element by the male tubular projection. The sealing element may comprise projections for securing the sealing element to the annular support wall. The sealing element may be glued to the common section. The sealing element may be glued to the annular support wall.

The container of the syringe may be a glass barrel. The male tubular projection may be made of glass. The syringe may be an OVS™-glass barrel syringe.

The syringe may be made of plastic. The container of the syringe may be made of plastic, e.g. COC.

Also, the first mechanical connection part may engage with the second mechanical connection part by means of a threaded connection, a snap-lock connection or a bayonet mount connection (bayonet lock).

In addition, the connecting element of the syringe assembly may be a syringe cover configured to cover the syringe. The syringe cover may only partly cover the syringe. The diameter of the syringe cover may be larger than the diameter of the syringe. A flange or collar of the syringe may be larger than the general diameter of the syringe cover. In this way it is possible to press the syringe flange or collar to the syringe cover, obtaining that a known position of the syringe in relation to the syringe cover is ensured.

Furthermore, the syringe cover may comprise a first cover part and a second cover part. The second cover part may lock the flange or collar of the syringe to a flange or collar of the syringe cover.

The second cover part may be configured to lock the syringe in relation to the first cover part by engaging a flange of both the syringe and the first cover part.

Also, the connecting element may comprise a first alignment element and the adaptor may comprise a second alignment element, indicating a fully engaged/locked state of the pharmaceutical adaptor system when aligned.

Moreover, the alignment elements may be integrated in the first mechanical connection part and the second mechanical connection part, respectively.

Further, the adaptor may comprise a unit connector adapted to connect the adaptor to the unit. The unit connector may be integrated in the adaptor.

Additionally, the unit may be a needle, a vial, a catheter or an IV line.

Furthermore, the adaptor may have a body, the body and the sealing element may be injection moulded in one mould by two component injection moulding.

The body may have a bore extending substantially perpendicularly to the axial extension.

In an embodiment, the sealing element may extend into the bore of the body. In this way the sealing element is kept in a fixed position in relation to the body of the adaptor. The sealing element may comprise areas of a larger diameter projecting from the outer surface of the sealing element. The sealing element may comprise projections on the outer surface. Seen in a cross sectional view perpendicular to the axial extension of the syringe assembly, e.g. the longitudinal axis, the sealing element may have altering thickness. In this way it is possible to increase the force subjected from the sealing element to the male tubular projection of the syringe.

Also, the body may have a first bore having an inner face, and the first bore of the body may extend from the inner face to the periphery of the body.

Further, the syringe assembly may have a tube part and a plunger which is slidable within the tube. The tube part of the syringe may be a container part.

Moreover, the sealing element may have a first fluid channel.

The male tubular projection may have a second fluid channel configured to fluidly connect the first fluid channel with the tube part of the syringe.

The male tubular projection may comprise a chamfering.

Furthermore, the first bore may comprise an end face, the male tubular projection may have an end face facing the unit, and when connected the end face of the first bore may have a distance to the end face of the male tubular projection.

In addition, the inner surface of an annular support wall may be provided with ribs or projecting parts to fixate the sealing element in relation to the annular support wall along the axial extension of the syringe assembly, i.e. the longitudinal axis.

Also, the sealing element may have a varying thickness along the axial extension.

The outer diameter of the male tubular projection may be larger than the inner diameter of the sealing element. In this way a firm sealing is achieved when the male tubular projection is inserted in the sealing element.

The inner diameter of the sealing element may overlap the outer diameter of the male tubular projection by 0.1 mm-1 mm, more preferred by 0.15 mm-0.8 mm, even more preferred by 0.2 mm-0.6 mm or more preferably by 0.25 mm-0.4 mm. In this way a tight connection between the male tubular projection and the sealing element is achieved.

In a connected state of the system, the male tubular projection of the syringe may axially extend, i.e. overlap, into the sealing element by 0.1 mm-10 mm or by 0.3 mm-9 mm or by 0.5 mm-8 mm or more preferred by 1 mm-5 mm. In this way it is achieved that the longitudinal tolerances, i.e. the manufacturing tolerances along the full axial extension of the syringe assembly, are fully compensated for in the sealing element. Furthermore, in this way both the tolerances of the syringe itself and e.g. a connection between the flange of the syringe and the syringe cover are fully compensated for when inserted in the sealing element. In this way, independently of the method connecting the syringe assembly and the adaptor and hence the unit, the user will experience a consistent user feedback, and hence a firm and uniform feeling of the connection even when with various units is achieved.

The present invention furthermore relates to a pharmaceutical kit system comprising a pharmaceutical adaptor system according to the present invention and an additional unit connected with an additional adaptor configured to be connected with the connecting element of the syringe assembly.

The pharmaceutical adaptor system as described above may be used for reconstitution. The pharmaceutical adaptor system may be a reconstitution kit.

Furthermore, the pharmaceutical adaptor system may be an in-line system for fluid communication from a syringe to a unit such as a vial.

Said syringe may be made of glass.

Moreover, the sealing element may be made of thermoplastic elastomer (TPE). In particular when manufacturing the sealing element by injection moulding, TPE is easy to use.

In an embodiment, the adaptor may have a thread on an outer face of the body configured to engage a thread of the connecting element of the syringe assembly.

Further, the syringe cover may have a window for inspection of the content of the syringe.

The adaptor may comprise a penetration element configured to penetrate a seal of the vial, e.g. a septum. The penetration element may be a spike. The penetration element may provide fluid communication from the vial to the syringe.

Moreover, the adaptor may have arms configured to engage the flange of the vial.

In addition, the first mechanical connection part of the connecting element may be the male part of the bayonet mount connection or the snap-lock connection and the second mechanical connection part of the adaptor may be the female part of the bayonet mount connection or the snap-lock connection.

Further, the male tubular projection may project further than the connection element along the axial extension.

Also, the connection element may have an outer face having an external thread and the adaptor may have an inner face comprising an inner thread configured to engage the outer thread.

BRIEF DESCRIPTION OF THE DRAWINGS

The invention and its many advantages will be described in more detail below with reference to the accompanying schematic drawings, which for the purpose of illustration show some non-limiting embodiments and in which FIG. 2A shows the pharmaceutical adaptor system of FIG. 1 in an assembled state, FIGS. 2B-2E show other embodiments of the pharmaceutical adaptor system shown in FIG. 1, FIGS. 3A-3C are enlarged views of a part of the adaptor system shown in FIG. 2A, where FIG. 3C is a partly cross-sectional view, FIGS. 4A-4C are enlarged views of a part of the adaptor system shown in FIG. 2B, where FIG. 4C is a partly cross-sectional view, FIG. 7C is a partly cross-sectional view, FIGS. 9A-9C are enlarged views of a part of the adaptor system shown in FIG. 8, where FIG. 9C is a partly cross-sectional view.

All the figures are highly schematic and not necessarily to scale, and they show only those parts which are necessary in order to elucidate the invention, other parts being omitted or merely suggested.

DETAILED DESCRIPTION OF THE INVENTION

Figure 1:
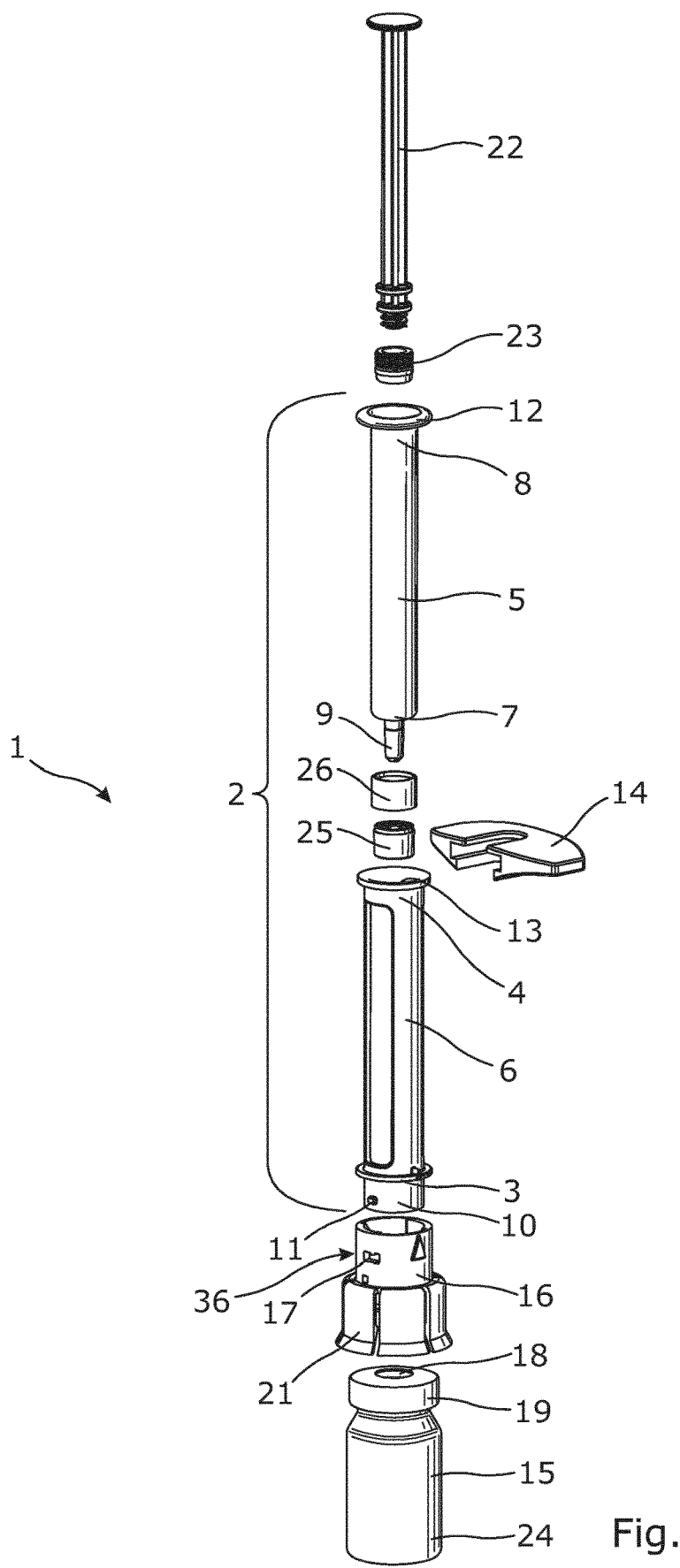
FIG. 1 shows an exploded view of a pharmaceutical adaptor system according to the invention.

FIG. 1 shows a pharmaceutical adaptor system 1 in an exploded view. The adaptor system 1 comprises a syringe assembly 2 comprising a syringe 5 and a syringe cover 6. The syringe assembly 2 has an axial extension and a first end part 3 and a second end part 4. The syringe assembly 2 is shown in exploded view, and it will be seen in FIG. 2A that the first syringe end part 7 and the second syringe end part 8 in an assembled state in fact is positioned at the first end part 3 and the second end part 4, respectively, of the syringe assembly 2. The first syringe end part 7 comprises a male tubular projection 9.

The syringe assembly 2 comprising a syringe 5 further comprises a connecting part 10 having a first mechanical connection part 11.

The syringe 5 comprises a syringe flange 12. The syringe cover 6 comprises a cover flange 13. In an assembled state, i.e. when the syringe 5 is inserted in the syringe cover 6, the syringe flange 12 and the cover flange 13 are kept abutting each other by a second syringe cover part 14, i.e. a flange lock part 14.

The pharmaceutical adaptor system 1 further comprises a unit 15. In this embodiment, the unit 15 is a vial 24 but the unit 15 may be a needle, a catheter or an IV line.

The pharmaceutical adaptor system 1 comprises an adaptor 16 comprising a body 36 providing fluid communication between the syringe 5 and the unit 15. The adaptor 16 comprises a second mechanical connection part 17 configured to engage with the first mechanical connection part 11 in an engagement direction, thereby in an engaged state preventing movement by the first and second mechanical connection parts 11, 17 along the axial extension. The adaptor 16 comprises a sealing element 42 (shown e.g. in FIG. 3C and FIG. 5) configured to receive the male tubular projection 9 of the syringe 5. In this embodiment, the unit 15 is a vial 24 comprising a septum 18 and a collar 19. The adaptor comprises fingers 21 arranged to lockingly engage with the collar 19 of the vial. The syringe 5 of the adaptor system 1 further comprises a stem 22 and a plunger 23 in order to eject a fluid from the syringe 5 or in order to fill the syringe 5 with fluid. The tubular projecting part 9 of the syringe 5 may be arranged with a Luer lock 25. The tubular projecting part 9 may be arranged with a support part 26 for supporting a cap, e.g. a protection cap, before use of the syringe 5. The syringe cover 6 has a window for inspection of the content of the syringe 5. The syringe of the syringe assembly comprises a tube part having a plunger which is slidable within the tube.

FIGS. 2A-2E show embodiments of the pharmaceutical adaptor system 1. The first mechanical connection part 11 and the second mechanical connection part 17 are shown in different embodiments, i.e. FIG. 2A and FIG. 2C show a bayonet lock, FIG. 2B and FIG. 2E show a threaded connection, and FIG. 2D shows a snap lock. It will be understood that the different embodiments of connecting the syringe assembly 2 to the adaptor 16 comprising a body 36 may be interchanged. FIGS. 2A, 2B, 2C and 2E all comprise a first visual alignment indicator 30 and a second visual alignment indicator 31.

FIG. 2A shows the system of FIG. 1 in an assembled state. It is seen that the syringe 5 is fully inserted in the syringe cover 6. The syringe 5 and the syringe cover 6 are locked together by the flange lock part 14, and the syringe assembly 2 is connected to the adaptor 16 by the first and second mechanical connection parts 11, 17. The fingers 21 of the adaptor 16 have engaged with the collar 19 of the vial 24.

The pharmaceutical adaptor system shown in FIG. 2A may be used for reconstitution. The pharmaceutical adaptor system may be part of a reconstitution kit.

FIG. 2B shows an embodiment of the pharmaceutical adaptor system 1 in which the syringe assembly 2 of the system 1 is arranged to be connected to a unit 15 in the shape of a needle 30. The syringe assembly comprises a first mechanical connection part interacting with the second mechanical connection part 17 (not visible) and a thread of the adaptor 16.

FIG. 2C shows an embodiment of the pharmaceutical adaptor system 1 similar to that of FIG. 2B, where the mechanical connecting parts 11, 17 form a bayonet lock.

FIG. 2D shows an embodiment of the pharmaceutical adaptor system 1 similar to that of FIG. 2B, where the mechanical connecting parts 11, 17 form a snap lock. In this embodiment, the syringe assembly 2 and the adaptor 16 are connected by forcing the adaptor along the longitudinal axis of the syringe assembly 2. Hence, in this embodiment, the syringe assembly 2 and the adaptor 16 do not need to be turned in order to be locked to each other. In order for the user to be assured that the syringe assembly 2 and the adaptor 16 are fully connected, the alignment indication is a sound, and hence the snap lock constitutes an audio alignment indication.

FIG. 2E shows an embodiment of the pharmaceutical adaptor system 1 configured with the same connection parts (not visible) as in FIG. 2B. This embodiment is shown having first and second visual alignment parts 31, 32 in order to indicate to the user that the adaptor system is fully connected, i.e. that the syringe assembly 2 and the adaptor 16 are fully engaged. This embodiment shows the unit 15 as a catheter or IV line 32.

FIGS. 3A-3C shows an enlarged view of the embodiment shown in FIG. 1 and FIG. 2A focusing on the parts near the adaptor 16.

FIG. 3A shows that the first and second visual alignment parts 30, 31 are aligned. The first and second mechanical connection parts 11, 17 are in their locked and fully connected position. The fingers 21 are formed as an integrated part of the adaptor 16. The fingers 21 are locked to the collar of the vial 24.

FIG. 3B shows the syringe assembly 2 separated from the adaptor 16. It is shown that guides 35 are arranged in the internal surface of the adaptor 16 in order to guide the first mechanical connection parts 11 to the second mechanical connection part 17 and form a bayonet lock. While forcing the syringe assembly 2 along the longitudinal axis of the syringe assembly 2 towards the adaptor 16, the mechanical connection parts 11 will slide on the guide 35 and the syringe assembly 2 will rotate around its central axis. A part of the guides 35 may be arranged in a plane which is substantially perpendicular to the longitudinal axis of the syringe assembly. When the first and second visual alignment indicators 30, 31 are aligned, the user is directly able to visually see that the adaptor 16 and the syringe cover 6 are fully connected. Furthermore, in this embodiment, the user will furthermore realise a tactile stop when the first mechanical connection part 11 is fully inserted in the second mechanical connection part 17. The second connection part 17 comprises a projection in order to form the bayonet lock. The sealing element 42 is shown inserted inside the annular support wall 40.

FIG. 3C shows a cross-sectional view of the adaptor 16 and the vial 24 of FIG. 3B. The projecting tubular part 9 of the syringe 5 is seen projecting beyond the first end part 3 of the syringe assembly 2, i.e. beyond the syringe cover 6 when following the longitudinal axis of the syringe assembly 2. It will be understood that the projecting tubular part 9 does not necessarily project beyond the syringe cover or syringe assembly 2. It is seen that the fingers 21 configured to attach the adaptor to the vial 24 (the unit 15) are integral with a body 36 of the adaptor arranged to receive the first end part 3 of the syringe assembly 2. In this embodiment, the body 36 of the adaptor 16 is partly an annular wall 37 and a common section 38 for interfacing to the unit 15, i.e. the vial 24. Arranged concentrically with the central axis of the syringe assembly 2, an annular support wall 40 is arranged having an internal surface 41. The internal surface 41 of the annular support wall 40 is configured to receive a sealing element 42. The sealing element 42 comprises an inner face 43 and an outer surface 44. The outer surface 44 of the sealing element abuts the internal surface 41 of the annular support wall 40. The inner face 43 of the sealing element 42 is configured to abut an outer face 45 of the male tubular projection 9. The sealing element 42 is a tubular element having a thickness and a length along the axial extension, said axial extension being larger than the thickness. The annular support wall 40 extends from the common section 38. In the present embodiment, a penetration element/spike 50 extends from the common section 38 arranged to be inserted through the septum 51 into the vial 24. In this way fluid communication is provided through the penetration element/spike 50 through the bore of the sealing element 42, and hence also along the centre bore of the annular support wall 40 to the chamber of the syringe 5 via the male tubular projection 9 (shown in more detail in FIG. 5). In the cross-sectional view of FIG. 3C body of the adaptor 16 is shown comprising a sealing element having two inlets 39 arranged in the bores. In this way the sealing element can be injection moulded directly when moulding the body 36. Hence the adaptor 16 will be manufactured directly as a two-component adaptor. The number of inlets 39 may be just one or a number of inlets, such as two, three, four or more. In a different manufacturing process the sealing element 42 may be inserted in a process successive to the moulding of the adaptor. The sealing element 42 may be made from a resilient material such as TPE. The resilience of the sealing element 42 provides that the sealing element subjects a force to the syringe assembly 2, forcing the syringe assembly 2 away from the adaptor 16. However, due to mechanical connection parts, the syringe assembly 2 and the adaptor 16 will remain connected. In this way the sealing element 42 is resiliently configured to provide an axial force opposite the engagement direction upon compression of the sealing element by the male tubular projection 9. The inlet 39, i.e. bore in the body 36, extends substantially perpendicularly to the axial extension of the syringe assembly 2. In this embodiment, the bore extends substantially perpendicular to the longitudinal axis of the syringe assembly. However, the bore/inlet may extend in an angle to the longitudinal axis.

FIGS. 4A-4C show an embodiment of a pharmaceutical adaptor system similar to that of FIGS. 3A-3C. In this embodiment, it is shown that the first and second mechanical connection parts 11, 17 are threads. It is seen that the syringe cover comprises a first visual alignment indicator 30 and the adaptor comprises a second visual alignment indicator 31. The unit 15 is, in this embodiment, a needle 29. Hence the adaptor 16 provides fluid communication from the syringe 5 to the needle 29. In the cross-sectional view in FIG. 4C it is seen that the common section 38, similar to that of FIG. 3C, connects the body of the adaptor 16 and the unit 15, i.e. the needle 29. The sealing element 42 is shown only having one perpendicular string of material i.e. the inlet 39 formed in the bore of the body.

In FIG. 4C, it is seen that the male tubular projection 9 of the syringe 5 has a larger outer diameter OD than the inner diameter ID of the sealing element 42. The sealing element 42 is an elastomer, and hence the annular wall of the sealing element will be forced outwards when the male tubular projection 9 is inserted in the sealing element 42 (shown in e.g. FIG. 5). The dimensions "OD" and "ID" are only shown on FIG. 4C, but it will be understood that the same relation is shown in e.g. FIG. 3C, FIG. 6C, FIG. 7C and FIG. 9C. The male tubular projection 9 may have a conical outline, and hence the dimension OD may preferably refer to the smallest dimension, e.g. at the tip of the male tubular projection, disregarding the chamfering. However, referring to both FIG. 4C and FIG. 5, it will be understood that even if referring to the dimension "OD" at the very tip of syringe, i.e. including any chamfering in the case where the syringe extends/is inserted a very small distance into the sealing element, the dimension of "ID" still needs to be smaller than "OD". It is seen that the body 36 of the adaptor 16 is prepared for two component injection moulding by having a bore 39 in which the sealing 42 is injected.

Figure 5:
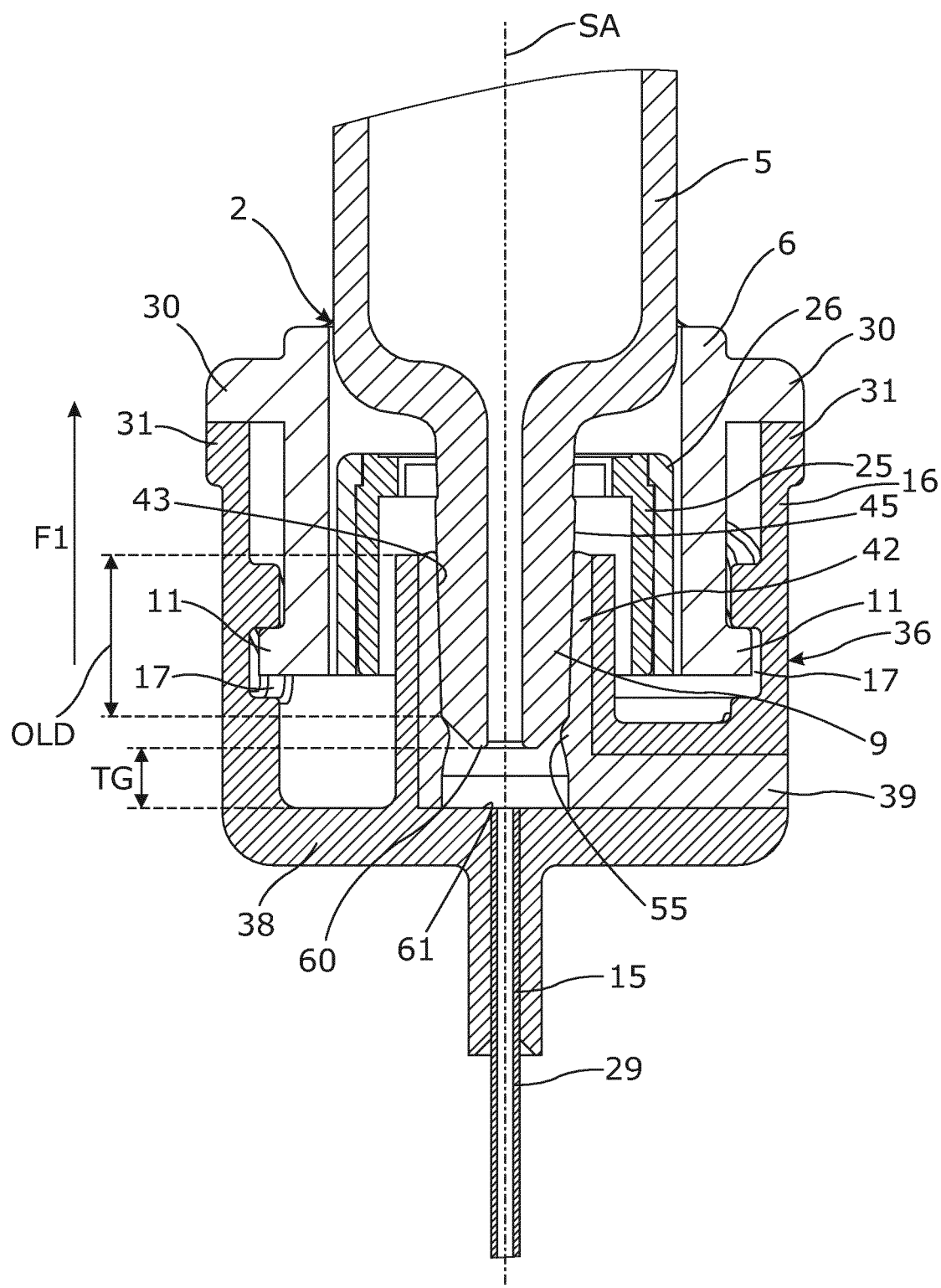
FIG. 5 shows a cross sectional view of the embodiment shown in FIG. 4A, FIGS. 6A-6C are enlarged views of a part of the adaptor system shown in FIG. 2C, where

FIG. 5 shows a cross-sectional view of FIG. 4A, i.e. having the syringe assembly 2 (only partly visible) fully inserted and connected to the adaptor 16. The first mechanical connection part 11 and the second mechanical connection part 17 are threaded connections. When turning the adaptor 16 and the syringe cover 6 in opposite directions, they either disconnect or connect. When connecting, the male tubular projection 9 of the syringe 5 is drawn into the centre part of the tubular sealing element 42. Thereby the outer surface 45 of the male tubular projection 9 of the syringe 5 is brought into contact with the inner face 43 of the sealing element 42. The sealing element 42 being resilient causes the sealing element 42 to be partly forced along the male tubular projection 9 of the syringe 5. Hence, a bead 55 is formed and the bead 55 subjects an opposite directed force F1 on the male tubular projection 9, i.e. the tip 60 of the syringe 5, along the longitudinal axis SA of the syringe assembly 2. The syringe 5 and the syringe cover 6 are connected at the flanges by the flange lock part 14 (not visible, see FIG. 2A), i.e. the second syringe cover part. The cross-sectional view of FIG. 5 shows the Luer lock part 25 and the support part 26 although they do not have any function in this embodiment. However, the adaptor system needs to take these parts into consideration since they may be mounted on the syringe as a standard feature. Hence, the adaptor shown in FIG. 5 has then necessary space for these parts. This eliminates that glass syringes often have tolerances that cause a connection to a device without a sealing element to be insufficiently fluid tight. It is seen that a gap, a tip gap TG, is present between the tip 60 and an inner passage surface 61 of the common section 38. The tip gap TG is present in order to allow for the overall length of the syringe 5 to vary. The sealing element 42 ensures that sealing against the outer surface 45 of the tubular male projection 9 is sufficient to ensure a fluid tight connection.

If the sealing was to be carried out directly on the tip of the syringe, it would necessitate the pressure against the tip to become very large because it should be able to compensate for tolerances in the length of the syringe. It is shown that the male tubular projection 9 of the syringe 5 is overlapping, i.e. is inserted in, the sealing element by an overlapping distance OLD. The overlapping distance needs to be greater than the combined tolerances of the syringe and/or the syringe assembly.

In a connected state of the system, the male tubular projection 9 of the syringe 5 should axially extend, i.e. overlap, into the sealing element by 0.1 mm-10 mm or by 0.3 mm-9 mm or by 0.5 mm-8 mm or more preferred by 1 mm-5 mm. In this way it is achieved that the longitudinal tolerances, i.e. the manufacturing tolerances along the full axial extension of the syringe assembly, are fully compensated for in the sealing element. Furthermore, in this way both the tolerances of the syringe itself and e.g. a connection between the flange of the syringe and the syringe cover are fully compensated for when inserted in the sealing element. In this way, independently of the method connecting the syringe assembly and the adaptor and hence the unit, the user will experience a consistent user feedback, and hence a firm and uniform connection is achieved.

Figure 6A:
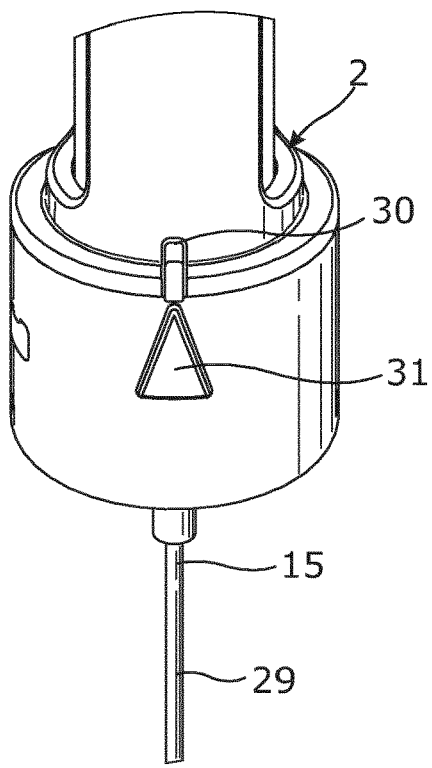
FIG. 6C is a partly cross-sectional view.
Figure 6B:
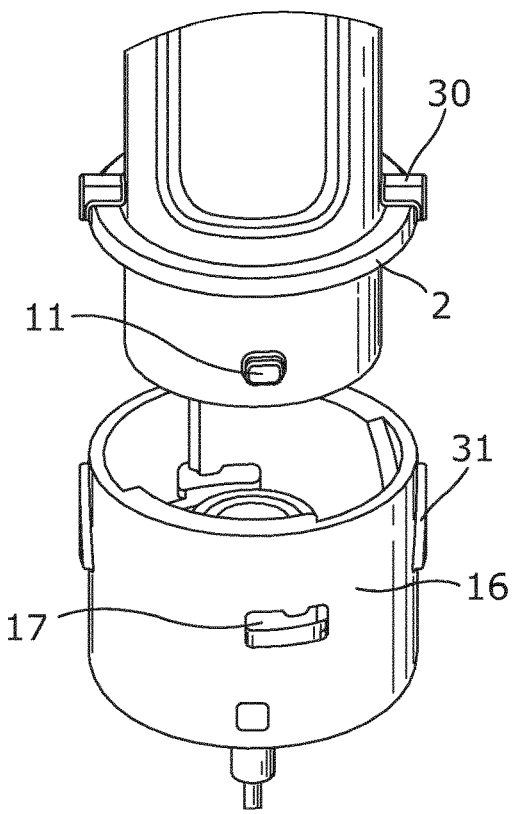
Figure 6C:
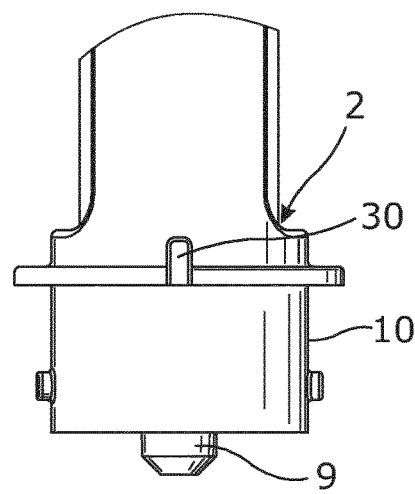
Figure 6C:
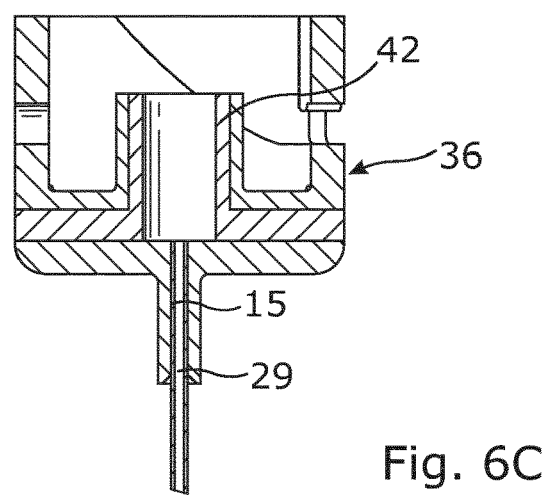

FIGS. 6A-C shows the adaptor system of FIG. 2C in an enlarged view similar to FIGS. 4A-C and FIGS. 3A-C. The mechanical connection between the syringe assembly 2 and the adaptor is carried out by bayonet coupling comprising the first mechanical part 11 and the second mechanical part 17. FIG. 6A shows a further embodiment of the second alignment indicator 31. In FIG. 6C it is seen that the body 36 similar to that seen in FIG. 5 and the syringe assembly comprises a connection part 10.

Figure 7A:
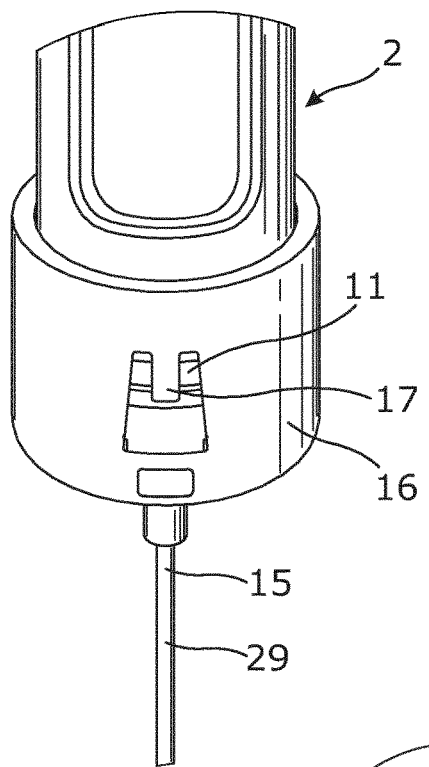
FIGS. 7A-7C are enlarged views of a part of the adaptor system shown in FIG. 2D, where
Figure 7B:
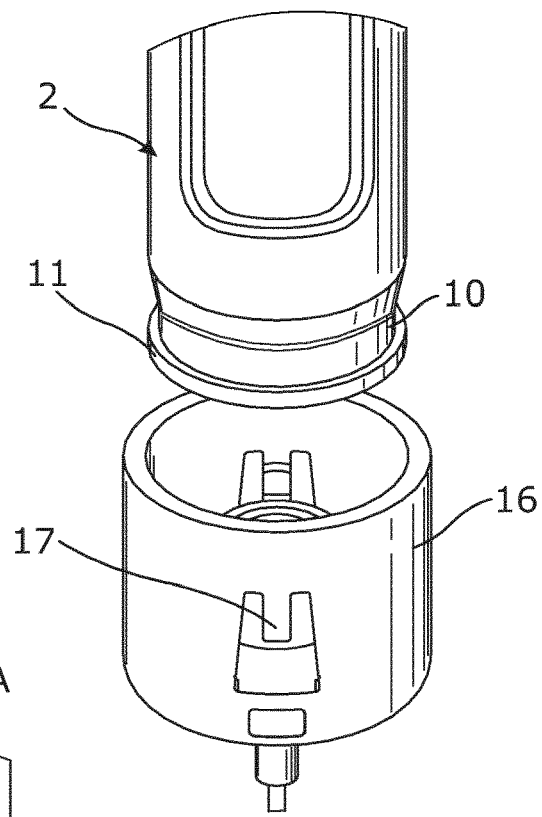
Figure 7C:
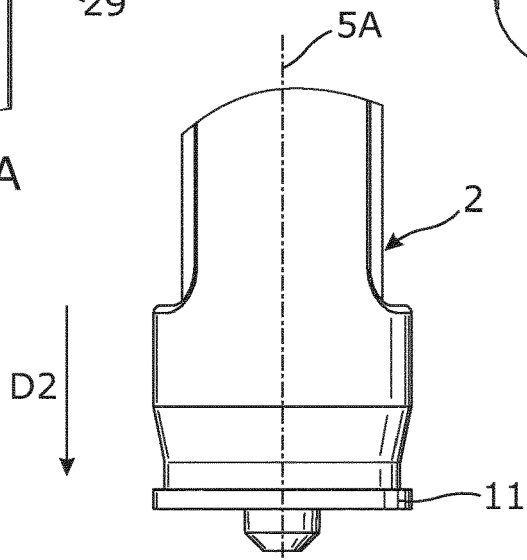
Figure 7C:
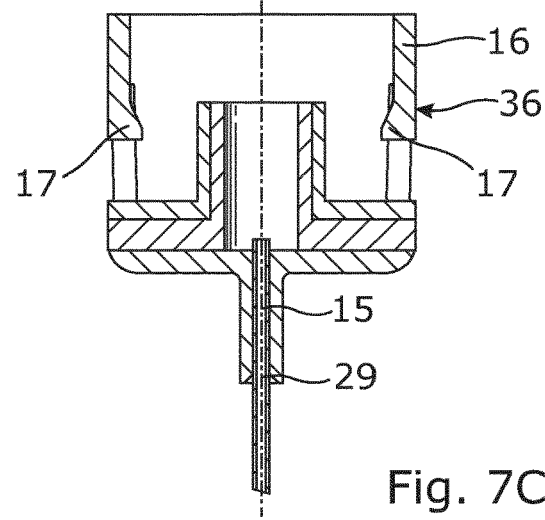

FIGS. 7A-C shows an enlarged view of the embodiment shown in FIG. 2D. This embodiment relies solely on a movement along the axial extension SA, shown in FIG. 7C, in the direction D2 in order to connect the syringe assembly 2 with the adaptor 16. The first end of the syringe assembly 2 comprises the connection part 10 (see FIG. 7B) and the first mechanical connection part 11 in the form of an annular projection. Upon insertion of the syringe assembly 2 into the adaptor 16, the annular projection lockingly interacts with the second mechanical connection part 17 and they constitute a snap lock. Since no turning of the syringe assembly 2 in relation to the adaptor 16 is required, the visual alignment indicators are left out. However, it will be understood that the visual alignment indicators could still be present. Instead of the visual alignment indicators the present embodiment provides an audio alignment indicator. This is achieved when the second mechanical connection part 17 has passed the annular projection 11, i.e. the first mechanical connection part 11. The second mechanical connection part 17 is forced to constitute a larger diameter when the annular projection 11, i.e. the first mechanical connection part 11, is forced to pass the second mechanical connection part 17. Simliar to other embodiments, the adaptor 16 comprises a body 36.

Figure 8:
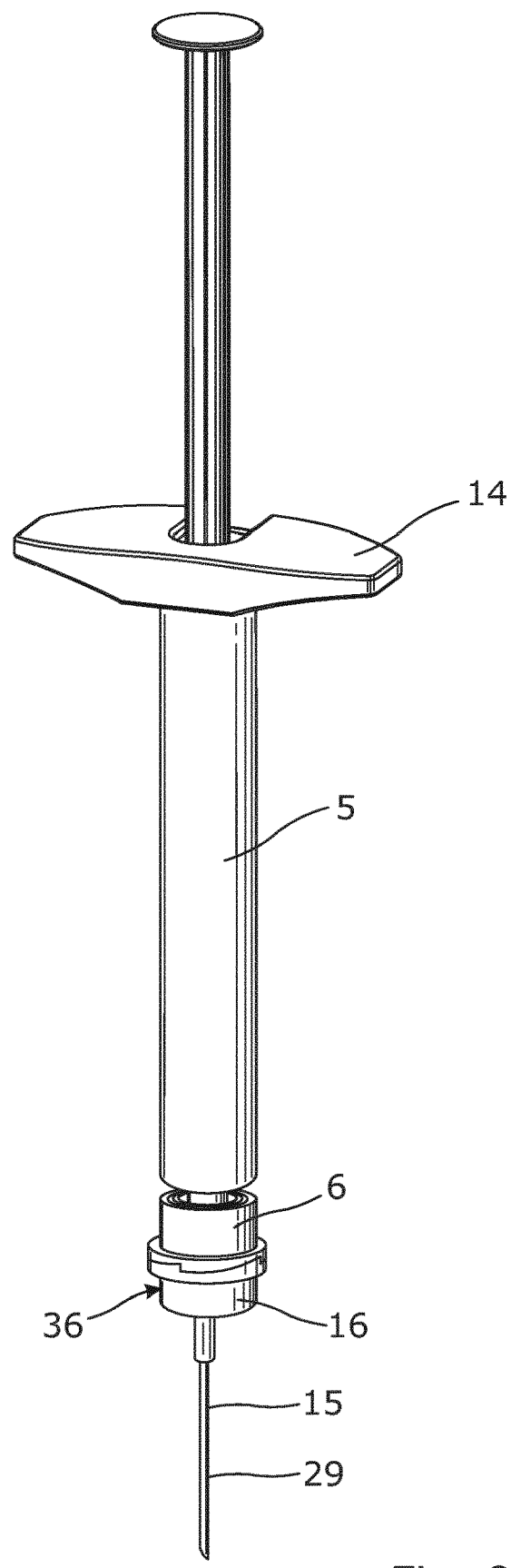
FIG. 8 shows a further embodiment of the pharmaceutical adaptor system according to the invention.

FIG. 8 shows a further embodiment of the invention in which the syringe cover 6 only covers the male tubular projection of the syringe 5. In order to provide a firm grip for the user, the second syringe cover part, i.e. the flange lock part 14, is still mounted to the syringe 5. The adaptor 16 comprises a body 36 and the adaptor 16 fluidly connects the syringe 5 with the unit 15 shown as a needle 29.

FIGS. 9A-9C show that the syringe cover 6 comprises a female Luer connection part 25. In this way the Luer coupling 25 may be used as the first mechanical connection part 11. The adaptor 16 comprising the body 36 further comprises an external thread as the second mechanical connection part 17. The thread is integrated in the outer surface of the annular support wall 40. The internal surface 41 (see FIG. 9C) of the annular support wall 40 abuts the outer face 44 of the sealing element 42. The connection element 17 has an outer face having an external thread, and the second connection element 11 on the adaptor 16 has an inner face comprising an inner thread configured to engage the outer thread i.e. the connection element 17. In this embodiment the syringe cover 6 primarily cover the male tubular projection of the syringe 5. The flange lock or second part of the syringe cover is omitted. The syringe cover 6 comprises a number of first tactile stops 71 and the adaptor comprises a number of second tactile stops 72. During connection of the syringe assembly and the adaptor, the user will turn the two parts until the first and second tactile stops meet each other, and the user can be confident that the part are fully and fluid tight connected.

Figure 10A:
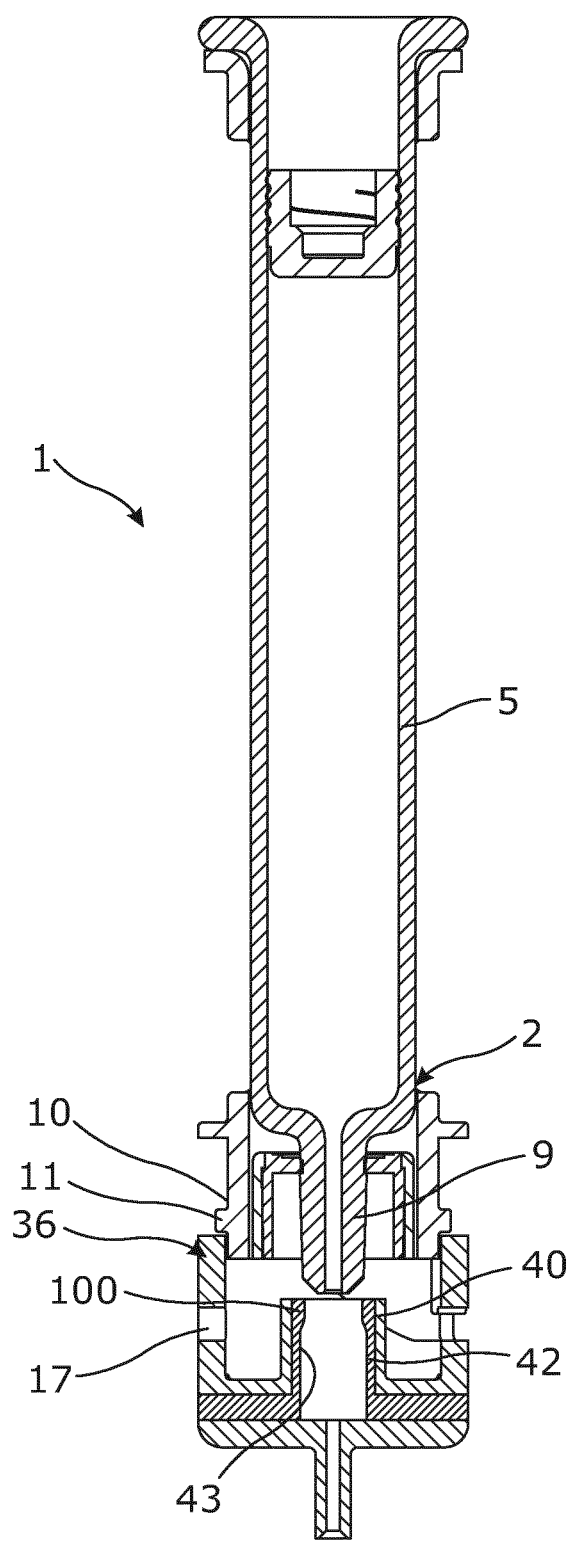
FIGS. 10A and 10B show an embodiment of the pharmaceutical adaptor system comprising a sealing element with an annular projection.
Figure 10B:
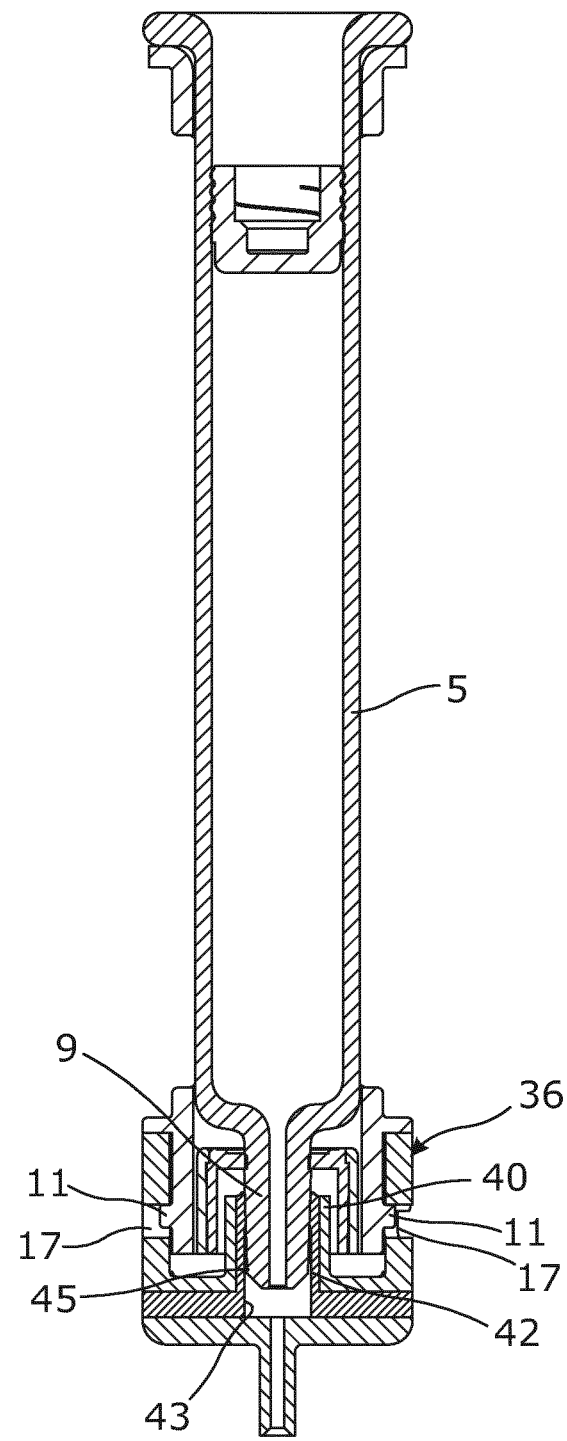

FIGS. 10A and 10B show an embodiment of the pharmaceutical adaptor system 1 comprising a positive stop similar to that shown in FIG. 3, i.e. a connection part 10 comprising a first connection part 11 and a second connection part 17. The embodiment shown in FIG. 10 shows a sealing element 42 comprising an annular projection 100. The annular projection 100 is projecting from the inner face 43 of the sealing element 42 and hence projecting inwardly, i.e. towards the common longitudinal axis of the pharmaceutical adaptor system.

In FIG. 10B it is shown that the annular projection 100 is forced radially outwards against the annular support wall 40. It is shown that a part of the sealing element 42 is forced slightly out of the volume defined by the annular support wall 42, i.e. past the upper rim of the annular support wall 42. The compressibility/elasticity of the sealing element 42 furthermore compensates for varying diameters of the male tubular part 9. It is seen that the first and second connection parts 11, 17 are locked together, and hence the pharmaceutical adaptor system has provided the user with at feedback that ensures full and hence correct assembly. In this embodiment it is directly visible for the user to see that the first connection part 11 is now visible in the second connection part 17. Furthermore, the user may turn the adaptor as hard as he desires because the first mechanical connection part 11 is forced against the wall of the second connection part 17 and there is no risk of applying too large a torque which could break the syringe 5. Hence, the first and second mechanical parts 11, 17 function as both visual indication and as a tactile stop and provide an audible "click" to let the user know that the correct assembly is achieved. Furthermore, the overlapping distance OLD discussed previously (in FIG. 5) can be smaller while still obtaining the same tight connection. Hence the pharmaceutical adaptor system shown in FIG. 10 compensates for large tolerances of the male tubular projection 9 of the syringe 5 and the sealing element. Hence, the pharmaceutical adaptor system provides a constant user feedback regardless of changes in their interrelated tolerances.

It will be understood that the sealing element as shown in FIG. 10 e.g. comprising an annular projection 100 may be used in all of the embodiments discussed above.

For all embodiments shown, the user feedback with respect to the connection state may be presented to the user, either visually, audibly, by a positive stop or by combinations thereof.

Although the invention has been described in the above in connection with preferred embodiments of the invention, it will be evident for a person skilled in the art that several modifications are conceivable without departing from the invention as defined by the following claims.

The invention claimed is:

1. A pharmaceutical adaptor system comprising:
a syringe assembly having an axial extension and comprising a first end part and a second end part, the first end part having a male tubular projection, the syringe assembly comprising a syringe and a connecting part having a first mechanical connection part, at least a portion of the first mechanical connection part having an inner surface spaced by a radial distance from and disposed radially outwardly of an outer surface of at least a portion of the male tubular projection,
a unit including at least one of a fluid dispensing element and a fluid storage element, and
an adaptor providing fluid communication between the syringe and the unit and having a second mechanical connection part, the inner surface of the at least a portion of the first mechanical connection part is disposed at least partially within and radially inwardly of at least a portion of the adaptor, the second mechanical connection part being configured to engage with at least a portion of an outer surface of the first mechanical connection part in an engagement direction when in a fully engaged position to at least temporarily prevent relative axial movement between the adaptor and the male tubular projection,
wherein the adaptor comprises a sealing element configured to receive the male tubular projection and provide sealing between the male tubular projection and the adaptor, wherein the sealing element comprises an inner surface configured to engage the outer surface of the male tubular projection, the inner surface of the sealing element facing radially inwardly prior to engaging the outer surface of the male tubular projection.

2. A pharmaceutical adaptor system according to claim 1, wherein the sealing element is a tubular element having a thickness and a length along the axial extension, said axial extension being larger than the thickness.

3. A pharmaceutical adaptor system according to claim 1, wherein the sealing element is resiliently configured to provide an axial force opposite the engagement direction upon compression of the sealing element by the male tubular projection.

4. A pharmaceutical adaptor system according to claim 1, wherein the first mechanical connection part engages with the second mechanical connection part by means of a threaded connection, a snap-lock connection or a bayonet mount connection.

5. A pharmaceutical adaptor system according to claim 1, wherein the connecting part of the syringe assembly is a syringe cover configured to cover the syringe.

6. A pharmaceutical adaptor system according to claim 1, wherein the connecting part comprises a first alignment element and the adaptor comprises a second alignment element, indicating a fully engaged/locked state of the pharmaceutical adaptor system when aligned.

7. A pharmaceutical adaptor system according to claim 6, wherein the alignment elements are integrated in the first mechanical connection part and the second mechanical connection part, respectively.

8. A pharmaceutical adaptor system according to claim 1, wherein the adaptor comprises a unit connector adapted to connect the adaptor to the unit.

9. A pharmaceutical adaptor system according to claim 1, wherein the fluid dispensing element is a needle, a catheter or an IV line and the fluid storage element is a vial.

10. A pharmaceutical adaptor system according to claim 1, wherein the adaptor has a body, the body and the sealing element being injection moulded by two component injection moulding.

11. A pharmaceutical adaptor system according to claim 10, wherein the body has a bore extending substantially perpendicularly to the axial extension.

12. A pharmaceutical adaptor system according to claim 11, wherein the sealing element extends into the bore of the body.

13. A pharmaceutical adaptor system according to claim 1, wherein the sealing element has a varying thickness along the axial extension.

14. A pharmaceutical kit system comprising a pharmaceutical adaptor system according to claim 1 and a second adaptor configured to be connected with the connecting part of the syringe assembly.

15. A pharmaceutical adaptor system according to claim 1, wherein the at least a portion of the first mechanical connection part comprises a wall at least partially surrounding the at least a portion of the male tubular projection.

16. A pharmaceutical adaptor system according to claim 15, wherein the wall is an annular wall.

17. A pharmaceutical adaptor system according to claim 1, wherein at least a portion of the adaptor is disposed radially between the at least a portion of the first mechanical connection part and the at least a portion of the male tubular projection.

18. A pharmaceutical adaptor system according to claim 1, wherein the at least a portion of the first mechanical connection part and the male tubular projection are not integrally formed as a single, unitary structure.

19. A pharmaceutical adaptor system according to claim 1, wherein an axial position of the at least a portion of the adaptor corresponds to an axial position of the at least a portion of the connecting part.

20. A pharmaceutical adaptor system according to claim 1, wherein the adaptor surrounds at least the at least a portion of the connecting part.

21. A pharmaceutical adaptor system according to claim 1, wherein the at least a portion of the first mechanical connection part is disposed radially between the at least a portion of the adaptor and the at least a portion of male tubular projection.

22. A pharmaceutical adaptor system according to claim 21, wherein the at least a portion of the first mechanical connection part does not directly contact and is not integrally formed with the male tubular projection.

23. A pharmaceutical adaptor system according to claim 22, wherein the at least a portion of the first mechanical connection part comprises a radially outwardly directed surface facing a radially inwardly directed surface of the at least a portion of the adaptor.

* * * * *

UNITED STATES PATENT AND TRADEMARK OFFICE
CERTIFICATE OF CORRECTION

PATENT NO. : 12,208,062 B2
APPLICATION NO. : 16/072767
DATED : January 28, 2025
INVENTOR(S) : Hans Stenberg Knudsen et al.

It is certified that error appears in the above-identified patent and that said Letters Patent is hereby corrected as shown below:

In the Claims

At Column 14, Line 13, "at least the" should be -- the --.

Signed and Sealed this
Twenty-fifth Day of November, 2025

John A. Squires
*Director of the United States Patent and Trademark Office*